(12) United States Patent
Mazor et al.

(10) Patent No.: US 11,517,365 B1
(45) Date of Patent: Dec. 6, 2022

(54) DEVICES AND METHODS FOR TREATMENT OF DERMATOLOGICAL CONDITIONS

(71) Applicants: Meital Mazor, Carlsbad, CA (US); Alexei V. Babkin, Albuquerque, NM (US)

(72) Inventors: Meital Mazor, Carlsbad, CA (US); Alexei V. Babkin, Albuquerque, NM (US)

( * ) Notice: Subject to any disclaimer, the term of this patent is extended or adjusted under 35 U.S.C. 154(b) by 1329 days.

(21) Appl. No.: 15/424,336

(22) Filed: Feb. 3, 2017

Related U.S. Application Data

(60) Provisional application No. 62/291,495, filed on Feb. 4, 2016.

(51) Int. Cl.
*A61B 18/02* (2006.01)
*A61B 18/00* (2006.01)

(52) U.S. Cl.
CPC ...... *A61B 18/02* (2013.01); *A61B 2018/0047* (2013.01); *A61B 2018/00452* (2013.01); *A61B 2018/0293* (2013.01)

(58) Field of Classification Search
CPC .......... A61B 18/02; A61B 2018/00577; A61B 2018/0212; A61B 2018/00041; A61B 2018/00357; A61B 2018/00791; A61B 2018/00863; A61B 2018/00989; A61B 2018/00994; A61B 2018/0172; A61B 2018/00023; A61B 2018/0293; F04C 2270/0421; F16L 13/103; F16L 15/00; F16L 2201/44; F16L 25/01; F16L 37/00; F16L 39/00; F17C 7/02

USPC ....................................................... 606/21–26
See application file for complete search history.

(56) References Cited

U.S. PATENT DOCUMENTS

| | | | |
|---|---|---|---|
| 6,083,222 A * | 7/2000 | Klein | A61B 18/1445 600/374 |
| 7,141,979 B2 | 11/2006 | Marek | |
| 7,789,849 B2 | 9/2010 | Busby et al. | |
| 2001/0029979 A1 * | 10/2001 | Zheng | F17C 13/025 137/240 |
| 2003/0109912 A1 * | 6/2003 | Joye | A61B 18/02 607/113 |

(Continued)

FOREIGN PATENT DOCUMENTS

EP    2856986 A1    4/2015

OTHER PUBLICATIONS

International Search Report in International Application No. PCT/US19/51746, dated Jan. 9, 2020.

(Continued)

*Primary Examiner* — Khadijeh A Vahdat
(74) *Attorney, Agent, or Firm* — Kim IP Law Group LLC

(57) ABSTRACT

Embodiments described herein are directed to a system for providing alternating freeze and thaw cycles. The system includes a controller, a vessel for holding a working fluid, a pressure generator, a cooler, a cooler heat exchanger, a heater, a heater heat exchanger, a check valve, and a treatment instrument. In some embodiments, the treatment instrument includes a distal end, a proximal end, a connecting portion adjacent to the proximal end, a needle element adjacent the distal end, a handle portion disposed between the proximal and distal end, and a depth-limiting element to limit an injection depth of the needle element.

7 Claims, 14 Drawing Sheets

(56) References Cited

U.S. PATENT DOCUMENTS

| | | | |
|---|---|---|---|
| 2003/0220674 A1 | 11/2003 | Anderson et al. | |
| 2004/0215294 A1* | 10/2004 | Littrup | A61B 18/02 607/96 |
| 2005/0187519 A1* | 8/2005 | Harris | A61M 25/0084 604/117 |
| 2006/0122590 A1* | 6/2006 | Bliweis | A61B 18/082 606/24 |
| 2008/0077202 A1 | 3/2008 | Levinson | |
| 2009/0118722 A1 | 5/2009 | Ebbers et al. | |
| 2010/0256621 A1* | 10/2010 | Babkin | A61B 18/02 606/21 |
| 2011/0306958 A1* | 12/2011 | Berzak | A61B 18/02 606/24 |
| 2012/0253336 A1* | 10/2012 | Littrup | A61B 18/02 606/21 |
| 2013/0190744 A1 | 7/2013 | Avram et al. | |
| 2014/0276698 A1* | 9/2014 | Wittenberger | A61B 18/02 606/21 |

OTHER PUBLICATIONS

Written Opinion in International Application No. PCT/US19/51746, dated Jan. 9, 2020.

* cited by examiner

DEVICES AND METHODS FOR TREATMENT OF DERMATOLOGICAL CONDITIONS

RELATED APPLICATIONS

This application claims the benefit of U.S. Provisional Application No. 62/291,595, filed Feb. 4, 2016, the entire contents of which are incorporated herein by reference in their entirety for all purposes.

BACKGROUND

Field

The disclosed and described technology relates generally to the thermal treatment of skin conditions. More specifically, embodiments of the present invention relate to systems, devices and methods for the treatment of skin conditions.

Description of the Related Technology

Human skin is the largest and most massive organ of the human body. Human skin consists of three layers: the epidermis, which is the outermost layer; the dermis, which is the middle layer and which contains vascular connective tissue, hair follicles and sweat glands; and the hypodermis, which is the subcutaneous adipose tissue. The epidermis is primarily composed of keratinocytes that produce keratins and intermediate filaments that provide mechanical stability. The dermis is largely composed of dense collagen-rich extracellular matrix (ECM). Dermal collagen represents the most abundant ECM protein and constitutes the bulk of skin (90% dry weight). (Uitto J. "Connective Tissue Biochemistry of the Aging Dermis. Age-Related Alterations in Collagen and Elastin," *Dermatologic Clinics* (1986) 4:433-446.) Dermal connective tissue collagen is essentially responsible for the skin's tensile strength and mechanical properties. In human skin dermis, collagen-rich ECM is synthesized, organized, and maintained by dermal fibroblasts. Therefore, impaired dermal fibroblast function has a significant impact on the properties of skin connective tissue.

Histological and ultrastructural studies have revealed that the major alterations in aged skin are localized in the dermal ECM. (Fisher G, Wang Z, Datta S, Varani J, Kang S, and Voorhees J. "Pathophysiology of Premature Skin Aging Induced By Ultraviolet Light," *New England Journal of Medicine* 337 (1997) 1419-28; Fisher, Varani, and Voorhees. "Looking Older: Fibroblast Collapse and Therapeutic Implications," *Archives of Dermatology* 144 (2008) 666-72.)

In young skin (20-30 years), intact collagen fibrils are abundant, tightly packed, and well-organized. In contrast, in aged skin (>80 years), collagen fibrils are fragmented and disorganized. Investigations have revealed that characteristic features of skin connective tissue aging are largely due to aberrant collagen homeostasis. Two interrelated mechanisms are involved; reduced collagen biosynthesis and increased collagen fibril fragmentation. These mechanisms result in net collagen deficiency, which manifests as thin, fragile skin. (Fisher G, Varani J, and Voorhees J. "Looking Older: Fibroblast Collapse and Therapeutic Implications," *Archives of Dermatology* 144 (2008) 666-72); Quan T, Shao Y, He T, Voorhees J, and Fisher G. "Reduced Expression of Connective Tissue Growth Factor (CTGF/CCN2) Mediates Collagen Loss in Chronologically Aged Human Skin," *Journal of Investigative Dermatology* 130 (2010) 415-24). Age-related aberrant collagen homeostasis impairs the structural integrity and mechanical properties of the skin, and contributes to age-related skin diseases.

Available Treatments for Skin Rejuvenation

A variety of treatment options for skin rejuvenation exist, from over-the-counter beauty products to surgical options such as face-lifts and everything in between. Many skin rejuvenation products work by hydrating or swelling the skin, temporarily providing a short-term reduction in the appearance of wrinkles. As soon as the swelling effect is gone, the original wrinkles return exactly as they were before treatment.

Energy based treatments, such as fractional laser treatments and High Intensity Focused radio-frequency (RF), claim to provide a more effective way to treat wrinkles having long-term results as compared to available over-the-counter products. These energy based treatments claim to work by creating controlled damage or trauma to skin thereby stimulating the body's natural healing response to rebuild damaged collagen and internal skin structure. (Hoon Kim J, Hee Min K, Yeong Heo C, Min Baek R, Jin Park H, Woong Youn S, and Hee Kim E. "Histological Evaluation of Dermal Tissue Remodeling With the 1444-nm Neodymium: Yttrium-Aluminum-Garnet Laser in in Vivo Model," *The Journal of Dermatology* 40.9 (2013) 706-10). This assumed mechanism of action (MOA) is very similar to the MOA of the derma rolling procedure, which involves rolling a small roller with fine needles over the skin. This then causes micro punctures in the skin, which lead to a puffy swollen face that is supposed to help with acne scarring and general skin damage. Once the skin is micro-punctured, new collagen is transported to the damaged areas. Because there is nothing to repair, the additional collagen helps to reduce wrinkles and other skin irregularities. These micro-punctures also allow creams/serums that are applied to the rolled areas to be more easily absorbed.

Freeze-Thawing Process on Skin

The effects of freezing the skin were described in clinical observations early in the 1990's. (Gage A. "History of Cryosurgery," *Seminars in Surgical Oncology* 14 (1998) 99-109). Physicians of that era were impressed by the good healing and lack of scarring after freezing skin lesions. Experiments with skin have confirmed this view. In experiments in rats, Li et al. produced full thickness wounds by hot thermal burns and by freezing for the purpose of comparing the difference in healing between the two modalities. (Li A, Chir, Ehrlich H, Trelstad R, Koroly M, Schattenkerk M, and Malt R. "Differences in Healing of Skin Wounds Caused by Burn and Freeze Injuries," *Annals of Surgery* 191.2 (1980) 244-48). The degree of tissue destruction with the two modalities was similar. The burn wound contained much more collagen than the freeze wound. The authors thought that slow removal and replacement of the collagen prevented the development of a contracted scar. A later study in rats again showed that the connective tissue matrix was important in controlling wound contraction. (Ehrlich H, Hembry R. "A Comparative Study of Fibroblasts in Healing Freeze and Burn Injuries in Rats," *The American Journal of Pathology* 117 (1984) 218-24.) In addition, experiments involving freezing the skin of pigs showed that fibroblasts were resistant to freezing and no fractures or dislocation of collagen fibrils were observed. (Shepherd J, Dawber R. "Wound Healing and Scarring After Cryosurgery." *Cryobiology* 21 (1984) 157-169.)

The resistance of collagen fibers in skin to damage from freezing is the basis for favorable healing. This healing is an active process that begins with an inflammatory reaction at the border of the lesion, induced by chemotactic factors. Early infiltration of neutrophils, then mononuclear cells, is stimulated by the mediators of inflammation, including prostaglandins, histamine, and cytokines. This cellular infiltration follows hypothermia and edema that develops with thawing of the frozen tissue. As a granulation tissue forms, fibroblasts differentiate into myofibroblasts and damaged collagen is replaced by new collagen. (Azzaniga S, Bravo A, Goldszmid S, Maschi F, Martinelli J, Mordoh J, and Wainstok R. "Inflammatory Changes After Cryosurgery-Induced Necrosis in Human Melanoma Xenografted in Nude Mice," *The Journal of Investigative Dermatology* 116 (2001) 664-71; Jiang J, Goel R, Iftekhar M, Visaria R, Belcher J D, Vercellotti G, and Bischof J. "Tumor Necrosis Factor-Alpha-Induced Accentuation in Cryoinjury: Mechanisms In Vitro and In Vivo," *Molecular Cancer Therapeutics* 7 (2008) 2547-55; Schacht V, Becker K, Szeimies R, and Abels C. "Apoptosis and Leucocyte-Endothelium Interactions Contribute to the Delayed Effects of Cryotherapy on Tumours In Vivo," *Archives of Dermatological Research* 294 (2002) 341-48.)

Effect of Cyclic Freeze-Thawing on Collagen

In further experiments, the effect of freeze-thawing cycles ("N") on the rheological and thermal properties of bovine skin collagen solution was investigated and resulted with increased collagen elasticity as N increased to 3, 5 and 7. Specially, after the freeze-thawing cycles of N=7, the recovery capacity of collagen remarkably increased (from 17.76% to 74.98%) and the hysteresis loop areas of collagen also became larger (from 95.53 to 218.24 Pa/s). In addition, as observed by atomic force microscopy, the fibers of collagen became thicker after the process of freeze-thawing cycles, indicating that the aggregation of collagen molecules was enhanced in the process of freeze-thawing. Meanwhile, the morphology of freeze-thawed collagen sponges examined by scanning electron microscopy exhibited a porous network structure with the pores becoming more regular with increasing freeze-thawing cycles, N. (Ding C, Zhang M, Li G. "Effect of Cyclic Freeze-Thawing Process on the Structure and Properties of Collagen," *International Journal of Biological Macromolecules* 80 (2015) 317-23.)

Accordingly, embodiments of the present invention are directed to using cryoablation systems and devices to freeze skin layers in order to stimulate collagen production as well as to produce other results in the skin layers.

SUMMARY

An aspect of the present invention is directed towards a system for providing alternating freeze and thaw cycles. In one embodiment the system includes a controller, a vessel for holding a working fluid, a pressure generator, a cooler, a cooler heat exchanger, a heater, a heater heat exchanger, a check valve, and a treatment instrument. In some embodiments, the treatment instrument includes a distal end, a proximal end, a connecting portion adjacent to the proximal end, a needle element adjacent the distal end, a handle portion disposed between the proximal and distal end, and a depth-limiting element to limit an injection depth of the needle element. The working fluid can be alcohol ethanol, octafluoropropane, diethyl ether or propylene glycol.

Another aspect of the present invention is directed to a treatment instrument for treating body tissue. The treatment instrument includes a distal end, a proximal end, a connecting portion adjacent the proximal end, a needle element adjacent the distal end, a handle portion disposed between the proximal and distal end, a depth-limiting element to limit an injection depth of the needle element into body tissue, and an adjustment device for adjusting the injection depth of the needle element. In some embodiments, the treatment device also includes a heating element.

A further aspect of the present invention is a method of treating skin conditions. In some embodiments the method includes identifying an area of skin tissue to be treated, inserting a needle portion of a treatment instrument into a first area of the skin tissue to be treated to a predetermined depth within the skin tissue, freezing the skin tissue adjacent the needle portion for a predetermined time, and immediately after freezing, thawing the skin tissue adjacent the needle portion for a predetermined time. Additional embodiments include that immediately after the thawing step, freezing the skin tissue adjacent the needle portion for a second time for a predetermined time and immediately after the second freezing is performed, thawing the skin tissue adjacent the needle portion for a predetermined time. After the freezing and thawing steps are completed for the first area of the skin, the method includes withdrawing the needle portion of the treatment instrument from the skin tissue in the first area and inserting the needle portion of the treatment instrument into a second area of the skin tissue to be treated to a predetermined depth within the skin tissue, freezing the skin tissue adjacent the needle portion for a predetermined time, and immediately after freezing, thawing the skin tissue adjacent the needle portion for a predetermined time.

The description, objects and advantages of embodiments of the present invention will become apparent from the detailed description to follow, together with the accompanying drawings.

BRIEF DESCRIPTION OF THE DRAWINGS

The above-mentioned aspects, as well as other features, aspects, and advantages of the present technology will now be described in connection with various embodiments, with reference to the accompanying drawings. The illustrated embodiments, however, are merely examples and are not intended to be limiting. Throughout the drawings, similar symbols typically identify similar components, unless context dictates otherwise. Note that the relative dimensions of the following figures may not be drawn to scale.

DETAILED DESCRIPTION

The disclosed and described technology relates to cryotherapy systems, devices and methods to treat various skin conditions.

The System and Treatment Instruments:

The system employs an open thermodynamic cycle and uses a cryogen that is a high-density fluid with a freezing temperature below the treatment temperature. The fluid should not be hazardous (such as toxic, explosive, etc.) and must have a high density in order for it to be an efficient thermal agent. The fluid should also have a low viscosity such that it can flow through small channels and small diameter lumens within the treatment device without a significant pressure gradient and/or viscous heating. Sample high density fluids for use in the present system are included in Table 1.

TABLE 1

| Fluid | Chemical Formula | Freezing Temperature (Celsius) | Equilibrium Pressure at 25° C. (MPa) | Density (kg/m$^3$) | Viscosity ($\mu$) at −25° C. (Pa · s) |
|---|---|---|---|---|---|
| Alcohol Ethanol | $C_2H_5OH$ | −114° | Stable | 890 | $4.0 \times 10^{-3}$ |
| Octafluoropropane | $C_3F_8$ | −150° | .087 | 1500 | $3.6 \times 10^{-4}$ |
| Diethyl Ether | $(C_2H_5)_2O$ | −116° | .100 | 750 | $2.0 \times 10^{-4}$ |
| Propylene Glycol | $C_3H_8O_2$ | −59° | Stable | 1050 | >0.04 |

Figure 1:
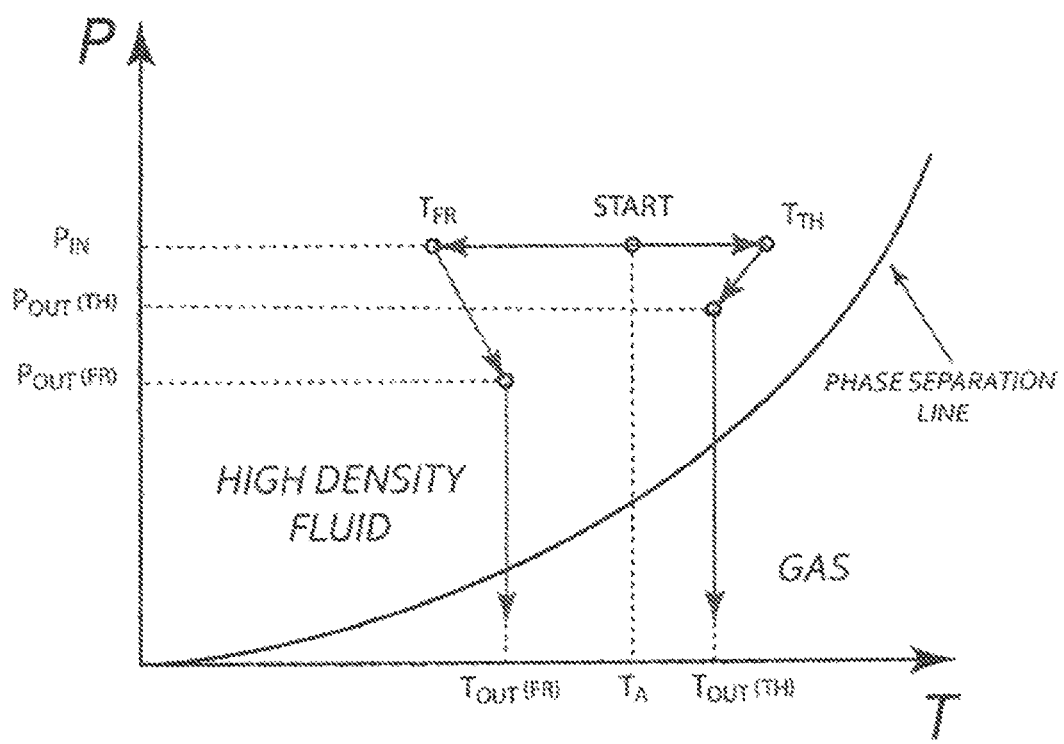
FIG. 1 is thermodynamic phase diagram of a working fluid for use in embodiments of the present invention.

Depicted in FIG. 1 is a simplified thermodynamic phase diagram of the working fluid of the present system. Shown in the figure are the two essential thermodynamic cycles that are required for the embodiments of the treatment methods disclosed and described herein: a Freeze Cycle (FC) and Thaw Cycle (TC). In the figure, the X-axis represents temperature (T) and the Y-axis represents pressure (P).

Initially, the working fluid is maintained at ambient temperature ($T_A$) and an elevated pressure ($P_{IN}$). Under these conditions, the fluid should be well within its high-density phase. Some examples of a fluid's high-density phase include the liquid phase and/or supercritical phase, which is where the fluid has the properties of both a liquid and a gas and which typically occurs above the liquid's critical point, i.e., above the liquid's critical temperature and critical pressure.

Figure 2:
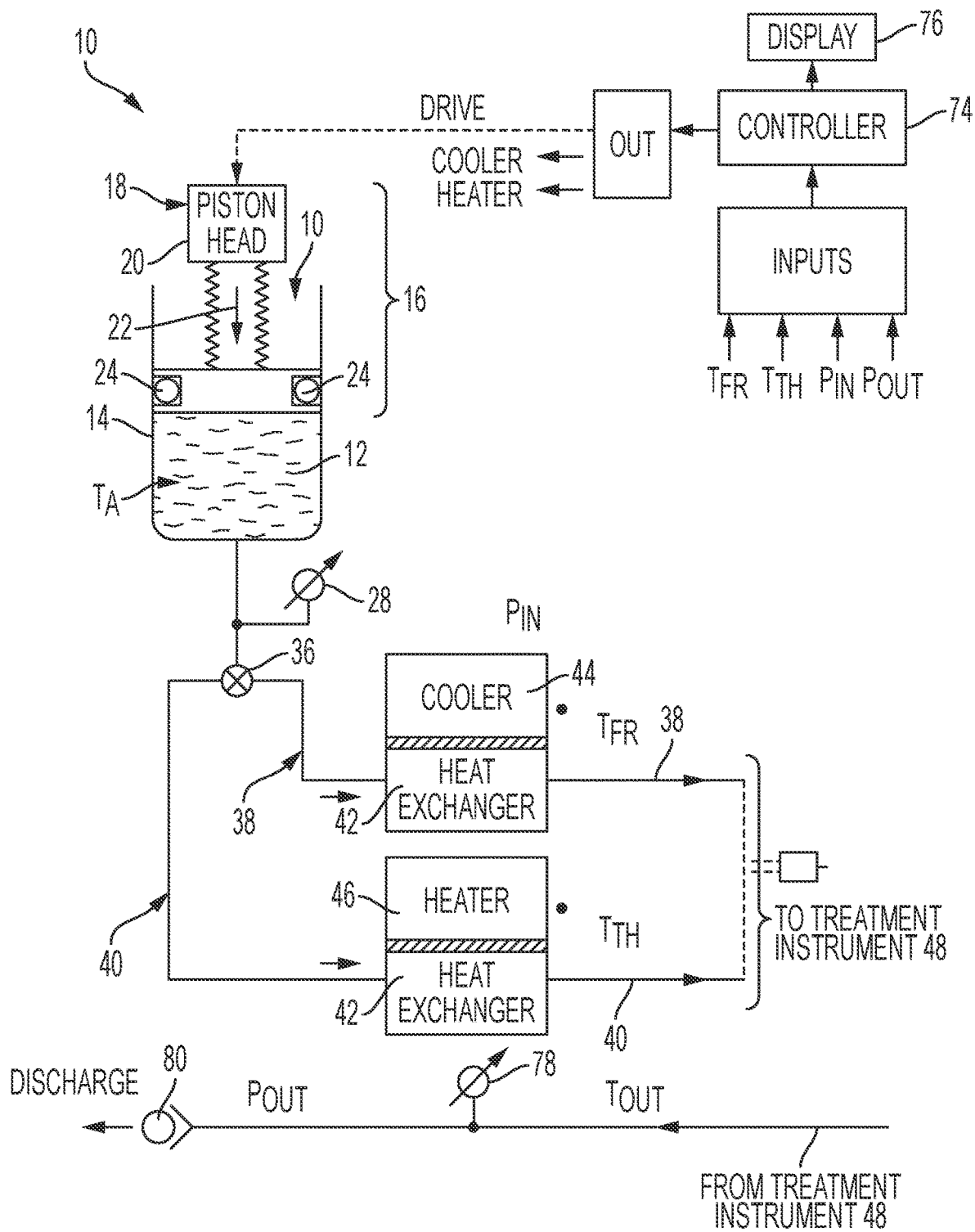
FIG. 2 is a schematic depiction of a system, according to an embodiment of the invention.

An embodiment of the cryotherapy system 10 is depicted in FIG. 2. Thermal fluid/cryogen 12 is held in a container 14 that is maintained at ambient temperature ($T_A$). The working pressure of the system 10 is maintained by a pressure generator 16. The pressure generator 16 can be any device that is capable of creating/generating the required working pressure for the thermal fluid and maintaining the required pressure for the flow rates required by the system. Non-limiting examples of pressure generators are described herein.

Figure 3:
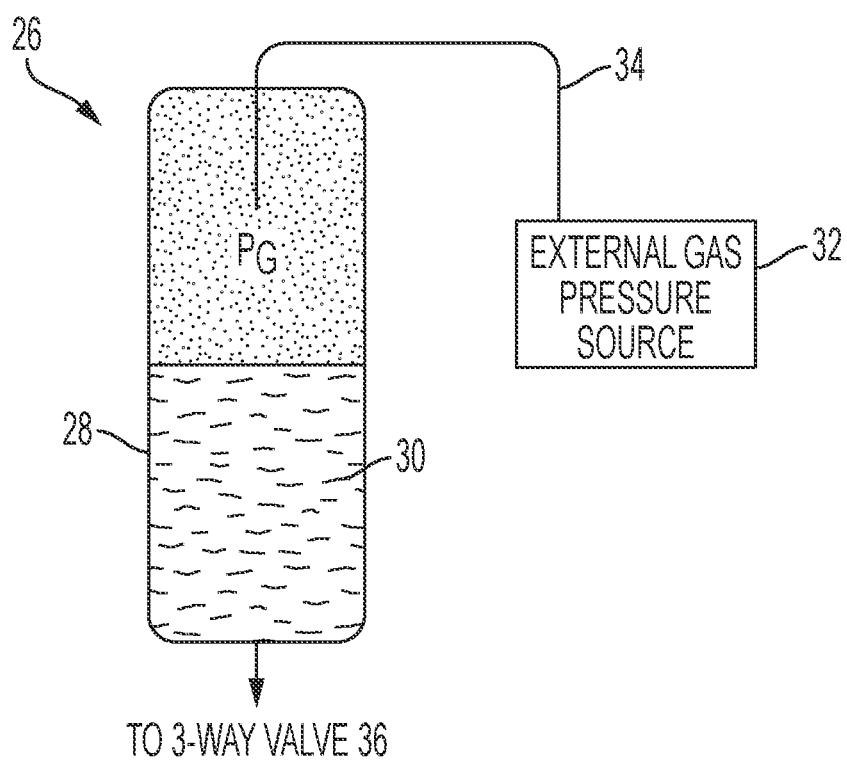
FIG. 3 depicts a pressure generator, according to an embodiment of the invention.

For example, the pressure generator can be a mechanical piston system 18 that includes a piston head 20, a connecting rod/means 22 and at least one compression ring/gasket 24. The piston head 20 and connecting rod 22 can be driven by, for example, an electrical (stepper) motor. The pressures necessary to run the system can also be generated and maintained with the use of a closed volume system that contains the working fluid. As depicted in FIG. 3, this type of closed volume system 26 includes a container/tank 28 to hold the working fluid 30, an external gas pressure source 32 and a pressure line 34 that connects the external gas pressure source 32 to the container/tank 28. In this system, pressurizing the external gas pressure source 32 to a certain gas pressure ($P_G$) also causes the working fluid 30 within the container/tank 28 to pressurize to a certain gas pressure ($P_G$). As will be readily apparent to those skilled in the art, other devices and means can be used to generate the required operating pressures of the system.

Because the system has a dual function of freezing and thawing, a dual fluid flow is included. This is achieved with the use of a three-way valve 36 as depicted in FIG. 2. In use, during a freezing cycle, the three-way valve 36 is actuated to direct working fluid flow along the cooling/freezing flow path 38, and during a thawing cycle, the three-way valve 36 is actuated to direct working fluid flow along the warming/thawing flow path 40. Thus, the three-way valve is used to control the freeze and thaw cycles of the system.

As can be seen in FIG. 2, both the cooling flow path 38 and the warming flow path 40 include heat exchangers 42 to thermally connect the working fluid to both a cooler 44 and a heater 46. The cooler 44 can be any type of cooling device capable of achieving and maintaining the required cooling/freezing temperatures. Example coolers 44 include, and are not limited to: thermoelectric coolers (TEC); cryocoolers such as the Pulse Tube, Stirling, Gifford-McMahon cooler, etc.; Joule-Thomson based coolers that use a gas or liquid supply; evaporative coolers such as refrigerators; and an immersion cooler with a cryogenic liquid. Another example of a cooler that can be used is an evaporative cooler that relies on cold temperatures that are generated by expansion of the high density thermal working fluid used in the present system as a result of the pressure drop in the check valve (discussed below). The heater 46 can be any type of a heating device capable of achieving and maintaining the required heating/thawing temperatures. Example heaters 46 include, and are not limited to: thermoelectric heater.

Also included with the system 10 is a treatment instrument 48 (for example, a needle device) for insertion into skin. The treatment instrument 48 connects to the system through a three-port hermetic connector that connects the cold fluid supply line, warm fluid supply line, and a return fluid line from the system 10 to the treatment instrument 48.

In some embodiments, multiple cold fluid supply lines and/or multiple warm fluid supply lines and/or multiple return fluid lines may be used.

Figure 4:
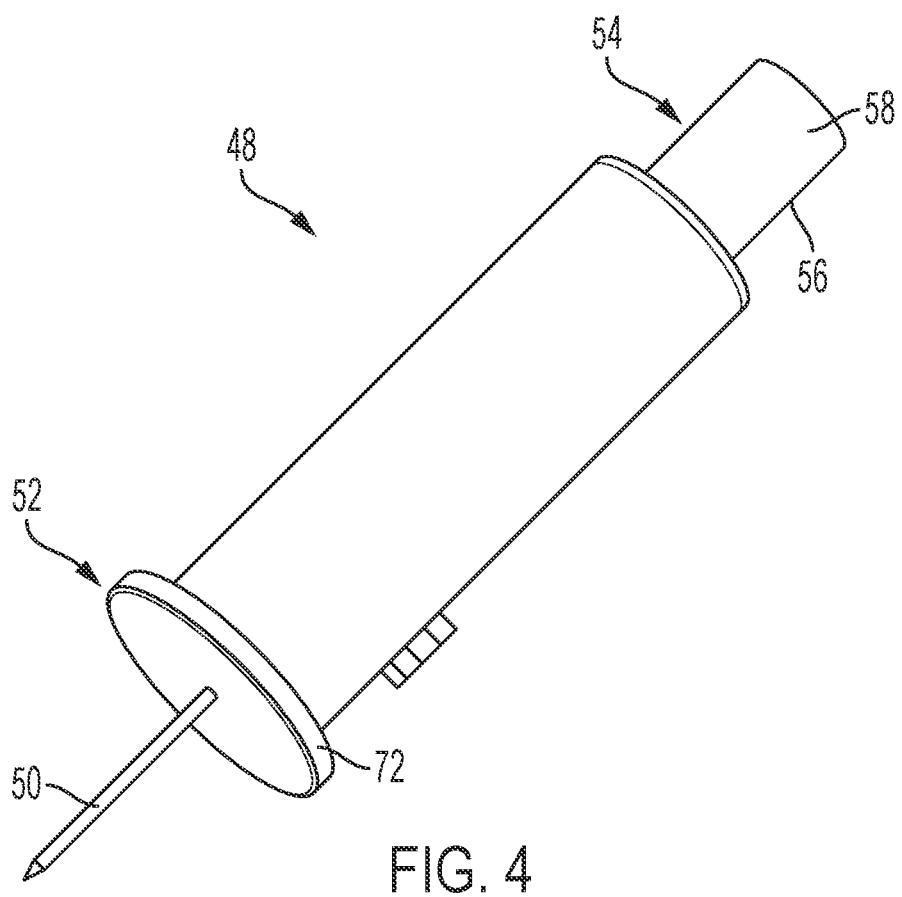
FIG. 4 depicts a treatment instrument, according to an embodiment of the invention.

Depicted in FIG. 4 is an embodiment of a treatment instrument 48. The treatment instrument 48 includes a small diameter needle 50 at its distal end 52. The needle 50 has a closed distal end with a flow chamber 53 to allow inflowing working fluid to flow through the treatment instrument 48. At its proximal end 54, the treatment instrument 48 includes a connecting portion 56 for thermally connecting to a supply line/hose 58 from the system 10. In some embodiments, the treatment instrument 48 connects to the system with a thermally insulated hose 58 that has at least two insulated lumens to deliver the high density working/thermal fluid to the treatment instrument (one lumen to deliver the cooling fluid and one lumen to deliver the warming fluid) and a lumen for the return flow. As an example, this thermal insulation can be made with Aerogel or it can be vacuum insulation. In order to prevent scarring, the needle 50 can be 27 gauge (or 0.4 mm diameter) and 10 mm length, for example.

Figure 5:
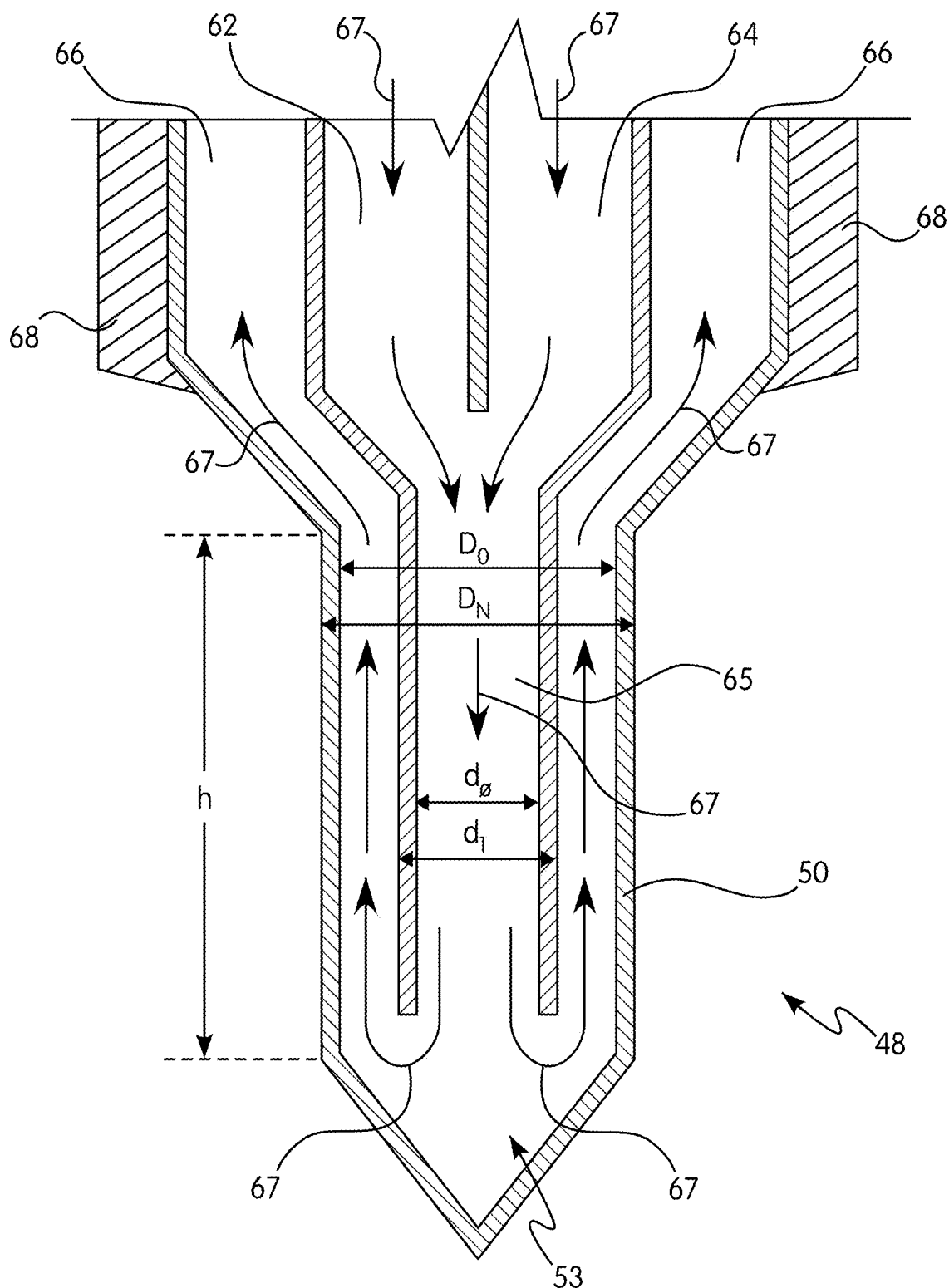
FIG. 5 is a cross-sectional view of a treatment device, according to an embodiment of the invention.

As shown in FIG. 5, the treatment instrument 48 can have a proximal section 60 of a larger diameter in order to house the cooling/freeze channel/lumen 62, the warming/thaw channel/lumen 64 and the fluid return channels/lumens 66. The cooling/freeze channel/lumen 62 and the warming/thaw channel/lumen 64 converge and open into a single delivery channel/lumen 65 for delivery to the flow chamber 53. Thus, as can be seen in FIG. 5, inflowing working fluid 67 (cooling or heating fluid) flows through either of the cooling/freeze channel/lumen 62 or the warming/thaw channel/lumen 64 depending on the treatment cycle (freezing/thawing), into the delivery channel/lumen 65, into the flow chamber 53 and then exits the flow chamber 53 by flowing into the return channels/lumens 66. In some embodiments, the proximal section 60 includes thermal insulation (vacuum, Aerogel, etc.) 68 to prevent heat loss and avoid moisture condensation and to prevent freezing/heating along this portion of the treatment instrument 48.

In some embodiments, the needle 50 length can range from approximately 1.0 mm to approximately 10.0 mm and extends form a handle portion 70 that, as depicted in FIG. 4, includes a disk-like section 72. The disk-like section 72 is intended to limit the depth that the needle 50 is inserted into the skin tissue under treatment. The insertion depth can be adjusted using a knob, slider, or a dial located on the handle 70. That is, the knob, slider, or dial can be used to either retract the needle 50 within the handle 70 thereby changing the length of the needle 50 that extends from the disk-like section 72. In some embodiments, the knob, slider, or dial can be used move the disk-like section 72 with respect to the needle 50, which also changes the length of the needle 50 that extends from the disk-like section 72. Although in the embodiment depicted in FIG. 4, the disk-like section 72 is shown in the form of a disk, the shape is not limited to a disk but can be any shape as long as it can prevent insertion of the needle 50 past section 72.

In some embodiments, the disk-like section 72 may include a heating element such as, for example, an electrical heater, that is used to prevent freezing of the upper most layer of skin (epidermis) by maintaining the temperature at a safe level, for example, approximately 30° C. to 42° C. The disk-like section 72 may also include a thermal sensor to monitor the temperature of the epidermis temperature in order to control the temperature of the heating element.

Following is a thermodynamic analysis for a needle 50 as depicted in FIG. 5. All of the thermodynamic properties and values used in the below analysis were from the National Institute of Standards and Technology's (NIST) Reference Fluid Thermodynamic and Transport Properties Database (REFPROP).

For the dimensions, assume a standard botox needle, which is 27 gauge. Such a needle can be constructed as follows:

Needle shaft (stainless steel): $D_N$=0.41 mm; $D_O$=0.25 mm
Inner tubing (polyimide): $d_1$=0.13 mm; $d_\sigma$=0.10 mm
Annulus space will have its hydraulic diameter ($d_H$) as follows:

$$d_H = D - d_1 = 0.12 \text{ mm OR } d_H \cong d_\phi$$

Because the preferred working fluid is octafluoropropane, assume:

TFR=−25° C., which leads to $\mu = 3.6 \times 10^{-4}$ Pa s

Assume laminar flow, for $\Delta P = P_{IN} - P_{OUT} = 100$ psi ($7 \times 10^5$ Pa)

$$Q = \frac{\Delta P \cdot \pi \cdot d_\phi^4}{128 \, \mu L} = \frac{(7 \times 10^5) \times (3.14) \times (10^{-16})}{(128) \times (3.6 \times 10^{-4}) \times 10^{-2}} \cong 5 \times 10^{-7} \, m^3/s$$

or $$30 \, cm^3/min$$

The corresponding Reynold's Number:

$$R_E = \frac{\rho v d_\phi}{\mu} = \frac{(1.5) \times (62 \times 10^{-4})}{(3.6 \times 10^{-4})} \cong 26$$

Accordingly, the flow is very laminar.

Cooling power=power required to warm up the needle to 0° C.:

$$W = Q \cdot \rho (H(0°C) - H(-25°C)); \text{ where } H \text{ is the enthalpy.}$$

$$W = \left(0.5 \frac{cm^3}{sec}\right) \times \left(1.5 \frac{g}{cm^3}\right) \times 24 \frac{J}{s} = 20 \frac{J}{s} = 20 \text{ Watts}$$

This amount of power is more than adequate for all skin/fat treatments discussed herein.

In some embodiments, the system may include multiple treatment instruments, which may be operated independently of one another or which may be operated synchronously. Accordingly, in these embodiments, the system will include multiple connection ports/supply hoses.

As depicted in FIG. 2, the system includes a controller/computer 74 for controlling/managing operation of the system 10. With the controller/computer 74, a user can input the operating parameters for the system 10 such as, for example, freeze temperature ($T_{FR}$), thaw temperature ($T_{TH}$), operating pressures ($P_{IN}$, $P_{OUT}$), freeze and thaw cycle run times, treatment cycles (freezing/thawing), number of cycles, treatment instrument operation, etc. The controller/computer 74 can be programmed with the operating parameters for different treatment procedures (as discussed below in more detail). Therefore, depending on the treatment procedure that will be performed, a user can simply choose that procedure from a library of procedures that has been programmed into the controller/computer 74 and the system will operate with the operating parameters that are specific for the subject procedure. The controller/computer 74 also allows a user to modify any such pre-programmed operating parameters for a treatment procedure based on personal preference, experience, treatment area conditions, etc. These modifications or changes to the operating parameters can be performed before a procedure commences or during a procedure based on how the procedure is progressing. Also included is a display 76 for displaying information relating to operation of the system 10 and any additional information essential for the treatment being performed.

Figure 6:
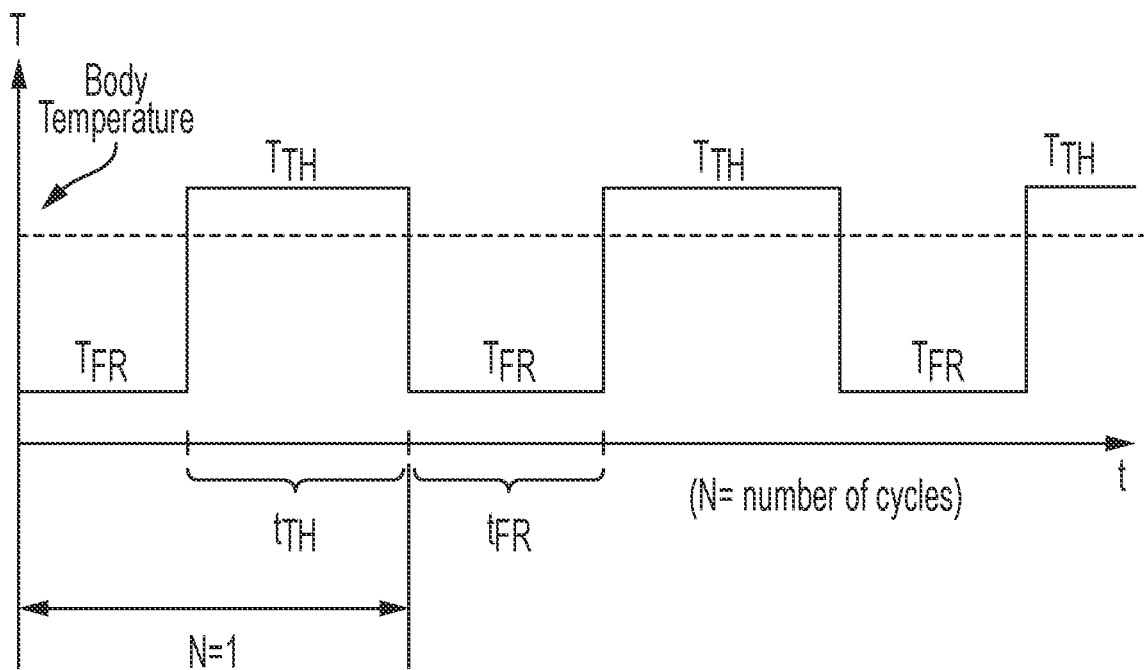
FIG. 6 depicts treatment cycles, according to an embodiment of the invention.

As depicted in FIG. 6, the treatment cycles of the system 10 consists of alternating periods of freezing ($T_{FR}$) and thawing ($T_{TH}$). Each period is characterized by its temperature (T), duration (t), and the number of duty cycles (for example, $T_{FR}$, $T_{TH}$, $t_{FR}$, $t_{TH}$, N). Thus, one cycle may include one freezing ($T_{FR}$) period for a set time ($t_{FR}$) and one thawing ($T_{TH}$) period for a set time ($t_{TH}$). The treatment cycles within one treatment can be identical or they may vary in temperature and/or duration.

In order to regulate the temperature for the freezing and thawing cycles, either of the following methods can be used. The freezing temperature ($T_{FR}$) can be maintained by setting the cooler 44 temperature to some constant value, −25° C., for example, and regulating the fluid flow by changing pressure $P_{IN}$ of the working fluid flowing from the container 14 to the cooler 44. Similarly, the thawing temperature ($T_{TH}$) can be maintained by setting the heater 46 temperature to some constant value, 38° C., for example, and regulating the fluid flow by changing pressure $P_{IN}$ of the working fluid flowing from the container 14 to the heater 46. Alternatively, the freezing temperature ($T_{FR}$) can be maintained by setting the pressure $P_{IN}$ of the working fluid flowing from the container 14 to the cooler 44 to a constant pressure and changing the temperature of the cooler 44. Similarly, the thawing temperature ($T_{TH}$) can be maintained by setting the pressure $P_{IN}$ of the working fluid flowing from the container 14 to the heater 46 to a constant pressure and changing the temperature of the heater 46. Either of the above methods may be used or a combination of the above methods may be used to regulate $T_{FR}$ and $T_{TH}$.

The system 10 may also include a plurality of sensors such as pressure gauges 78 and thermistors that are used to monitor operation of the system 10 and to control the operating parameters for treatment procedures. Information obtained from these sensors can be displayed on the display 76 so that a user has real-time operating data for the system.

In some embodiments, the system 10 includes a flow meter in the working fluid cooling/freezing flow path 38 in order to measure fluid flow through the system and hence the system's cooling power.

Operation of the system 10 will now be described. The working fluid 12 is first added to container 14, where it is then pressurized by the pressure generator 16 to a predetermined pressure ($P_{IN}$). Next, for a freeze cycle, the three-way valve 36 is actuated to open the flow path 38 to the cooler 44. The working fluid 12 is then delivered to the heat exchanger 42 for the cooler 44 where the working fluid 12 is cooled to a pre-set treatment freeze temperature ($T_{FR}$). Once the working fluid 12 is cooled to $T_{FR}$, the working fluid 12 is delivered the thermally insulated hose 58 to the treatment instrument 48, which is inserted into the target tissue to be cooled/frozen. Because the needle 50 of the treatment device 48 is in thermal contact with the target tissue, heat is removed from the target tissue by the flowing, cooled working fluid, thereby cooling/freezing the target tissue. Within the treatment device 48, the working fluid 12 flows into freeze channel/lumen 62, into the delivery channel/lumen 65, into to the flow chamber 53, then exits the flow chamber 53 by flowing into the return channels/lumens 66 and then exits the treatment device 48 through the return channels/lumens 66. Upon exiting the treatment device 48 through the return channels/lumens 66 and return lumen in the thermally insulated hose 58, the return flow of working fluid, which is now at a higher temperature ($T_{OUT}$) and lower pressure ($P_{OUT}$) than it was before flowing through the treatment instrument 48, is delivered back to the console, which houses many of the system's components, and discharged to the atmosphere via a check valve 80 that is pre-set to a certain release pressure ($P_C$). Using a check valve with a pre-set release pressure is required in order to maintain the working fluid in its high-density state throughout the freeze cycle. The pre-set release pressure ($P_C$) of the check valve 80 is determined by the choice of working fluid that is used in the system 10. That is, different pressures are required to be maintained for different working fluids in order to maintain the working fluids in their high-density state. It is important to note that from the time the working fluid 12 is pressurized and leaves the container 14 until the time it is discharged to the atmosphere through the check valve 80, the working fluid 12 always remains in its high density state as can be seen in FIG. 1. The flow rate of the working fluid 12 through the system 10 is determined by the difference between its initial pressure $P_{IN}$ and the pressure $P_{OUT}$.

The thaw cycle is similar to the freeze cycle except that the flow path of the working fluid 12 in the system 10 is different. For the thaw cycle, the three-way valve 36 is actuated to open the flow path 38 to the heater 46. The working fluid 12 is then delivered to the heat exchanger 42 for the heater 46 where the working fluid 12 is heated to a pre-set treatment thaw temperature ($T_{TH}$). Once the working fluid 12 is heated to $T_{TH}$, the working fluid 12 is delivered to the thermally insulated hose 58 to the treatment instrument 48, which is inserted into the target tissue to be heated/thawed. Operation of the system 10 for all other aspects is similar to that of the freeze cycle. Again, as shown in FIG. 1, the working fluid remains in its high-density state at all times during the thaw cycle while flowing in the system 10 until the check valve 80.

In another embodiment, the system can be a closed loop system. As used herein, "closed loop" means that instead of venting working fluid through a check valve to the atmosphere after it flows through the treatment instrument for either freezing or thawing, the working fluid is instead returned to the holding container for re-use by the system. This can be achieved by means of an external pump.

It is important to note that unlike prior systems (argon-based systems, for example), the cooling/freezing and warming/thawing effect in the present system does not occur at the treatment device. Instead, cooling and heating of the working fluid 12 are achieved using a dedicated cooler or heater prior to the working fluid entering the treatment device.

Treatment Methods

Treatment procedures using the disclosed and described systems and treatment devices will now be described. As previously discussed, the treatment instrument includes a sharp needle that is thin enough to be able to penetrate through the epidermal skin layer without leaving a scar behind and thick enough to expose all skin layers together or separately (epidermis 108, dermis 110 and hypodermis 112, as identified in the figures) to one or more freeze-thaw cycles. After the needle is inserted into the skin into the target tissue, a freeze cycle is begun, which can last a few seconds to few minutes, to freeze the target tissue to between approximately 0° C. to approximately −30° C. Following the freeze cycle, a thaw cycle is commenced exposing the target tissue to higher temperatures of between approximately 37° C. to approximately 45° C. in order to induce a fast heating/thawing process of the target tissue. Such freeze-thaw cycling stimulates biological effects such as the recovery of existing collagen, production of new collagen and establishment of new vasculature, all of which lead to skin rejuvenation. This biological response will be increased if this freeze-thaw cycling is repeated multiple times on the same skin area/target tissue.

This freeze-thaw cycling treatment in the dermal layer recovers existing collagen elasticity, collagen volume and collagen structure in a facial or body skin areas. Thus, the freeze-thaw cycling treatment can be applied directly to skin wrinkles or scared tissue to recover "old" collagen and reverse the aging process of the treated skin because recovering collagen elasticity, increasing collagen volume and recovering collagen structure reduces wrinkles and even causes wrinkles to disappear.

Freeze-thaw cycling in the dermal layer also promotes the production of new collagen. Because skin dermis is resistant to minor freezing injury, such as that produced by short cyclic exposure to temperatures of approximately −20° C., this procedure will result in no tissue loss or permanent damage and will heal quickly. The immediate and fast thawing of the tissue following the freeze induces this healing process, which includes cellular infiltration followed by hypothermia and edema leading to the formation of granulation tissue in which fibroblasts differentiate into myofibroblasts and damaged collagen will be replaced by new, healthy collagen.

The freeze-thaw cycling treatment in the dermal layer will also lead to the establishment of new vasculature. With aging, a progressive reduction of dermis vasculature occurs due to a reduction in the number and size of vascular vessels, which is associated with the progressive alterations of vascular wall components. These alternations advance until the function of the vessel ceases. (Bonta M, Daina L, and Mutiu G. "The Process of Ageing Reflected by Histological Changes in the Skin," *Romanian Journal of Morphology and Embryology* 54 (3 Suppl.) (2013) 797-804.) The exposure of the dermal layer to the freeze-thaw cycles results in cellular infiltration, which leads to the establishment of new vasculature. New vasculature is critical to the repair process of the devitalized tissue. (Gage A. "Experimental Cryogenic Injury of the Palate: Observations Pertinent to Cryosurgical Destruction of Tumors," *Cryobiology* 15 (1978) 415-25; Gage A, Greene G, Neiders M, and Emmings F. "Freezing Bone Without Excision. An Experimental Study of Bone-Cell Destruction and Manner of Regrowth in Dogs," *Journal of the American Medical Association* 196 (1966) 770-74.)

Direct exposure of the dermal layer to freezing temperatures is safe as long as the treatment does not lead to tissue necrosis in the skin epidermal layer. Tissue necrosis in the dermal layer is prevented by heating the epidermal layer in the vicinity where the freezing is occurring thereby keeping this layer in a temperature range (above approximately −10° C.) which should not cause any damage to the epidermal tissue. Heating can be performed by a heating element included on the treatment instrument such as is described above with respect to the disk-like section.

Figure 7:
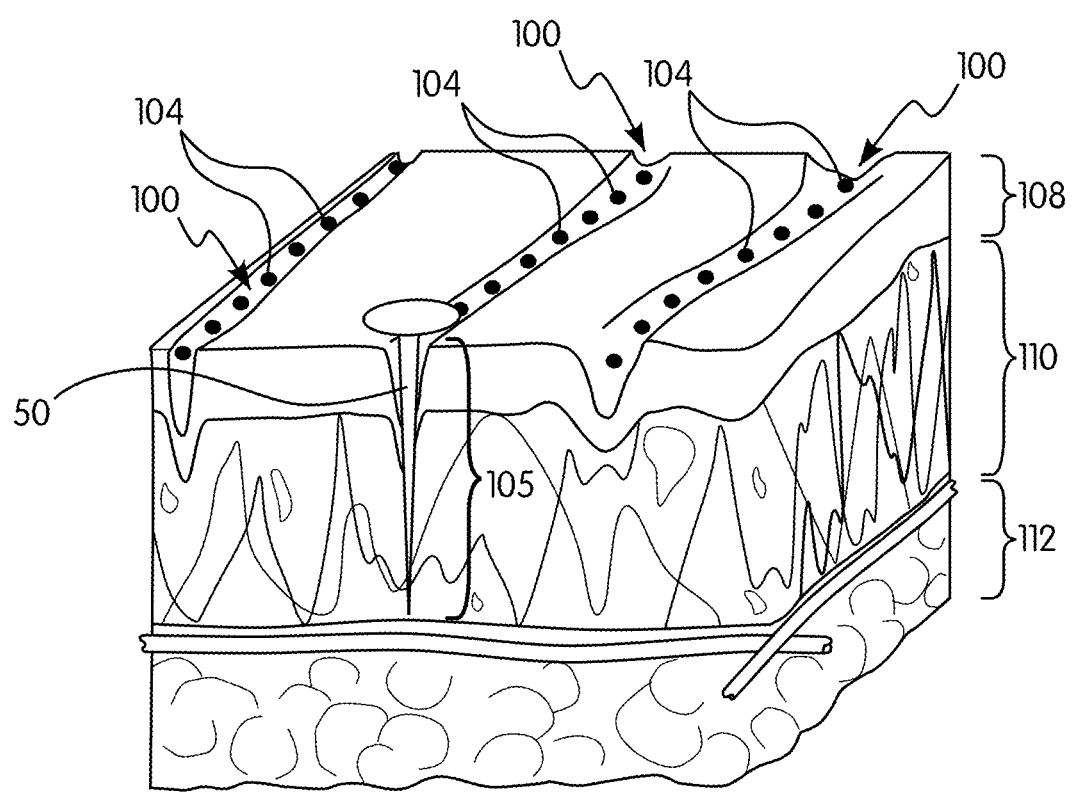
FIG. 7 depicts a procedure to treat wrinkles, according to an embodiment of the invention.
Figure 8:
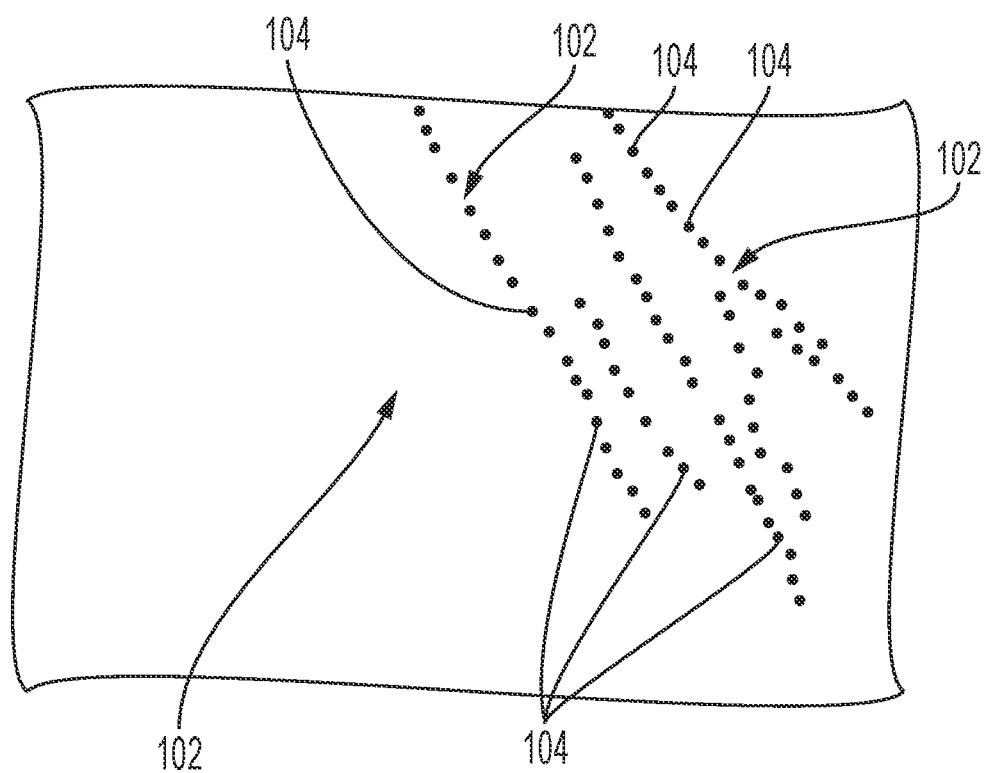
FIG. 8 depicts a procedure to treat stretch marks, according to an embodiment of the invention.

In order to transform aged (skin with wrinkles, for example), unhealthy skin and/or injured skin into healthier skin that is more elastic and that has a younger appearance, the system disclosed and described herein is used to apply multiple freeze-thaw cycles along wrinkle lines 100 (see FIG. 7), stretch marks 102 (see FIG. 8) and scar lines. As can be seen in FIGS. 7 and 8, multiple needle insertions 104 are performed along the wrinkle lines 100 and stretch marks 102. For each insertion 104, at least one freeze-thaw cycle is performed. To induce a higher healing response from the target skin tissue (that is, to promote new collagen production), multiple freeze-thaw cycles are performed for each needle insertion 104. The depth 105 of the needle insertion is based on the treatment procedure being performed as treating different skin conditions (wrinkles, pigmentation, etc.) requires stimulation of the healing response in the different skin layers (epidermis, dermis and hypodermis).

Depicted in FIG. 9 is a treatment directed towards treating abnormal skin pigmentation. Abnormal skin pigmentation such as, for example, sunspots on the skin, is a focal increase of skin pigment called melanin. Because of UV exposure, the pigment-making cells, called melanocytes, produce excess pigment in concentrated areas on the skin instead of uniformly across the skin surface. Importantly, with sunspots, there is no increase in the number of the melanocyte cell, only the pigment that they produce increases.

Figure 9A:
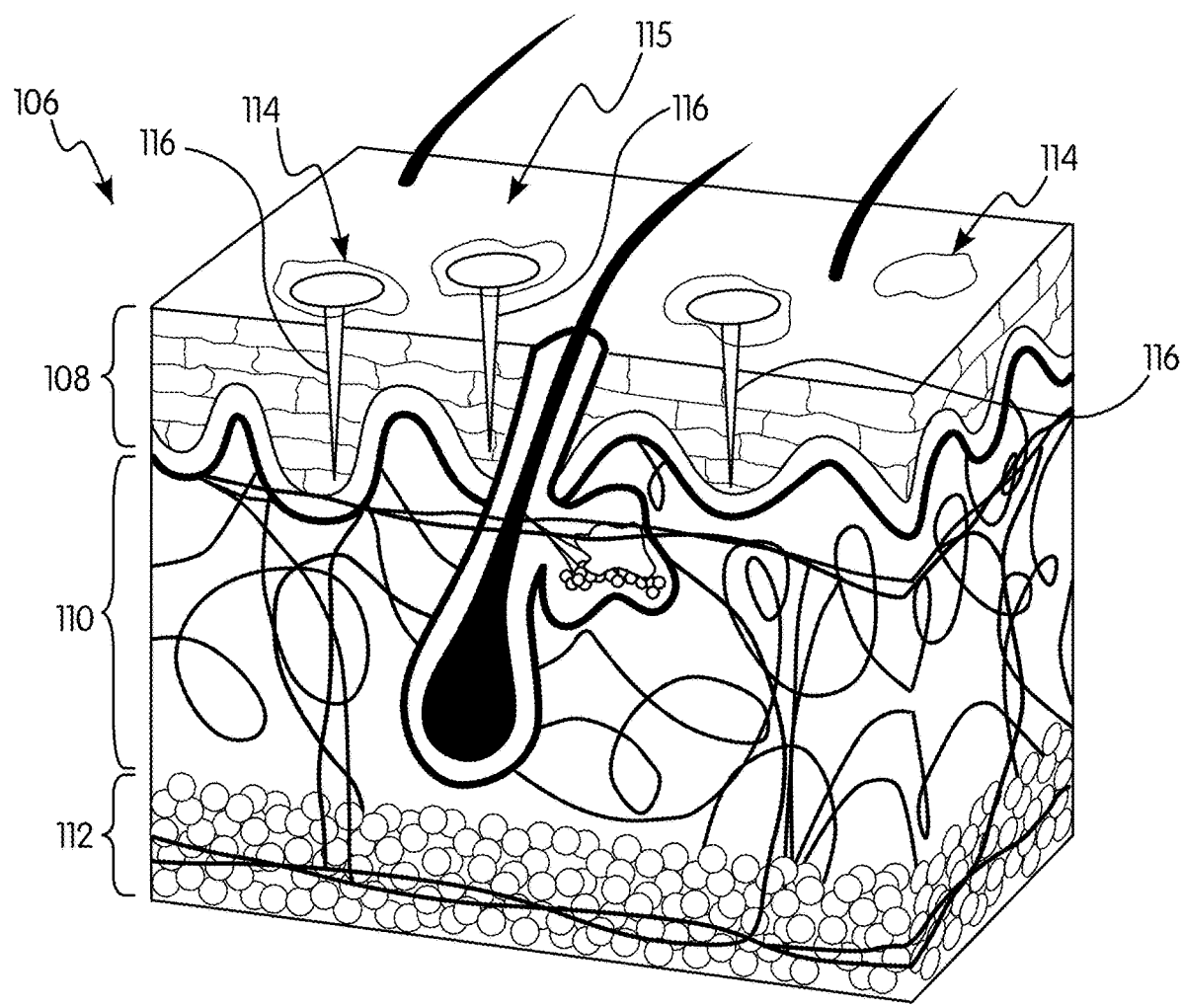
FIG. 9A depicts a procedure to treat abnormal skin pigmentation, according to an embodiment of the invention.
Figure 9B:
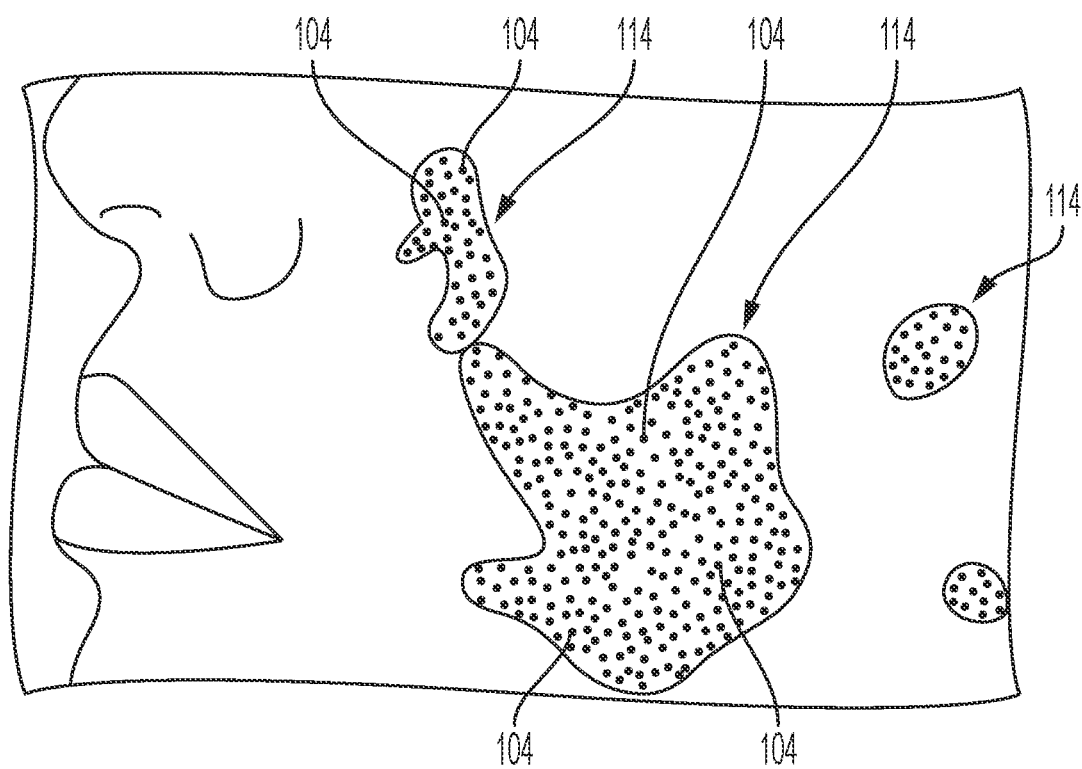
FIG. 9B depicts a procedure to treat abnormal skin pigmentation, according to an embodiment of the invention.

As can be seen in FIG. 9A, the skin portion 106 includes the epidermis 108, which is approximately 0.5 mm thick, the dermis 110 and the hypodermis 112. The abnormal skin pigmentation (sunspots) 114 extends form the surface 115 of the epidermis 108 into the thickness of the epidermis. Performing the freeze-thaw cycles in the epidermal layer 108 will lead to a reduction of the abnormal skin pigmentation as a result of reduced tyrosinase activity and melanin synthesis. (See Kim D, Park S, Kwon S, Joo Y, Youn S, Sohn U, Park K. "Temperature Regulates Melanin Synthesis in Melanocytes," *Archives of Pharmacal Research* 10 (2003) 840-45.) Performing the freeze-thaw cycles directly into the epidermal layer 108 and not only on the top surface 115 of the skin layer, allows a warmer freezing temperature to be used to remove the pigmentation completely and easily instead of using a colder freezing temperature solely on the surface. For surface only freezing, colder temperatures are needed to ensure that the tissue freezes into the thickness/depth of the epidermal layer 108. Use of a warmer freezing temperature results in reduced adverse events and scaring, if any. Thus, as can be seen in FIG. 9A, the needle portion 116 of the treatment device is inserted into the skin in the area of the abnormal skin pigmentation 114 to a depth of approximately 0.5 mm such that the effects of the freeze-thaw cycles are experienced along the entire thickness of the epidermis 108. Multiple needle insertions 104 can be performed at each area of abnormal skin pigmentation 114 as depicted in FIG. 9B. For each needle insertion, multiple freeze-thaw cycles can be performed to promote an increased and more robust healing response.

Figure 10:
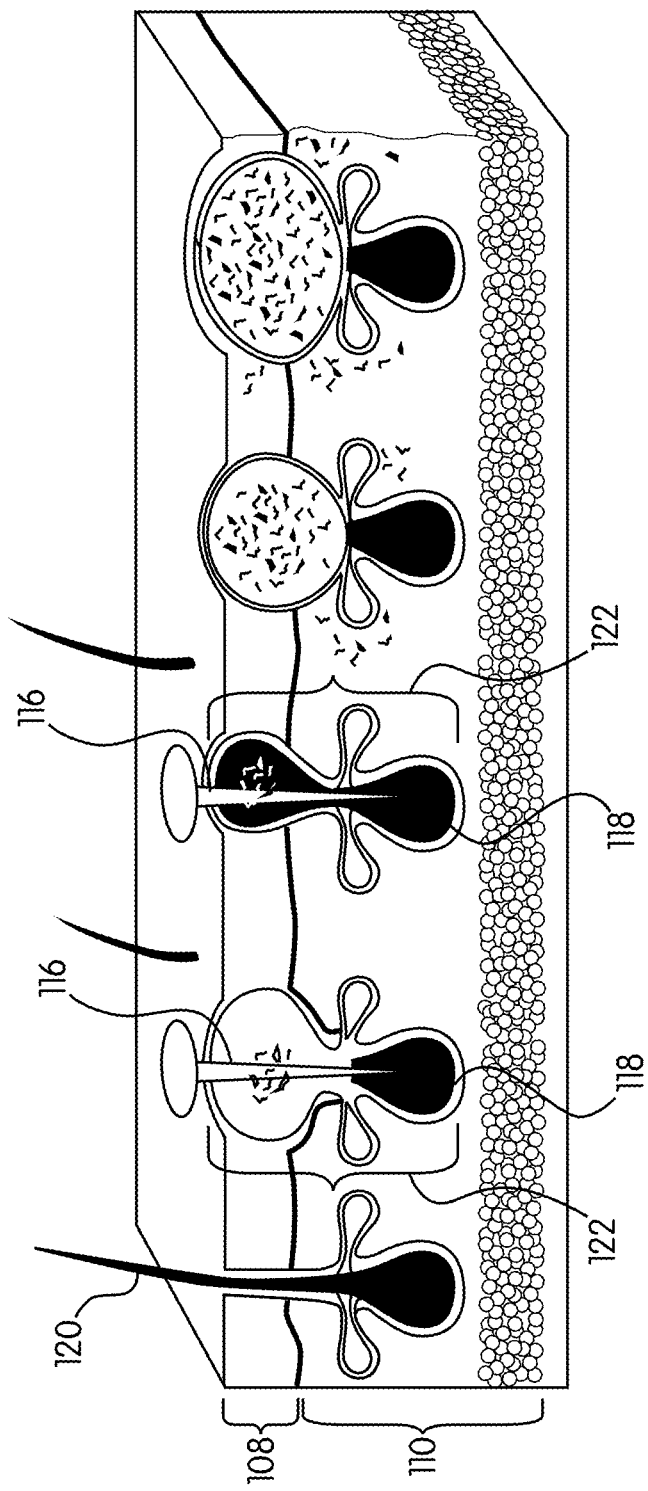
FIG. 10 depicts a procedure to treat acne pimples, according to an embodiment of the invention.
Figure 11B:
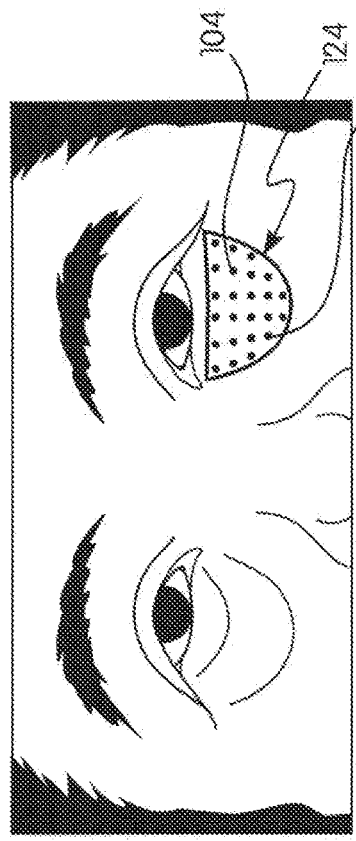
FIG. 11B depicts a procedure to treat bags under the eyes, according to an embodiment of the invention.
Figure 11D:
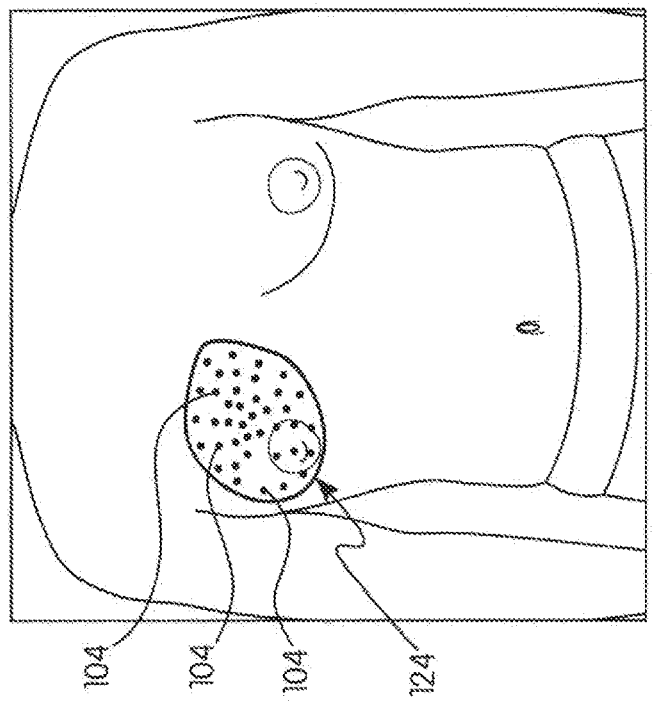
FIG. 11D depicts a procedure to treat enlarged male breasts, according to an embodiment of the invention.
Figure 11A:
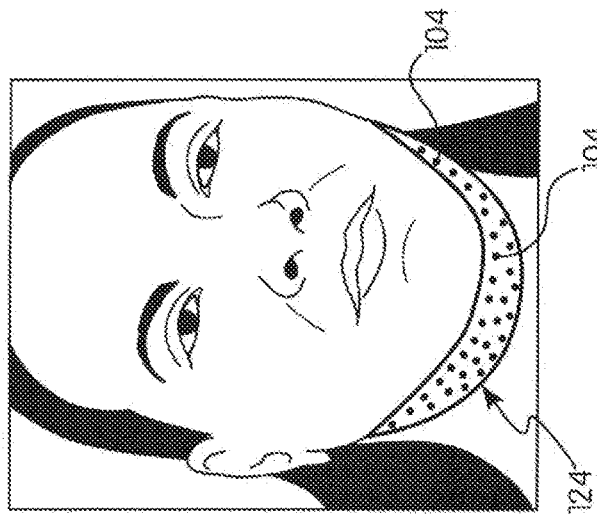
FIG. 11A depicts a procedure to treat double chin conditions, according to an embodiment of the invention.
Figure 11C:
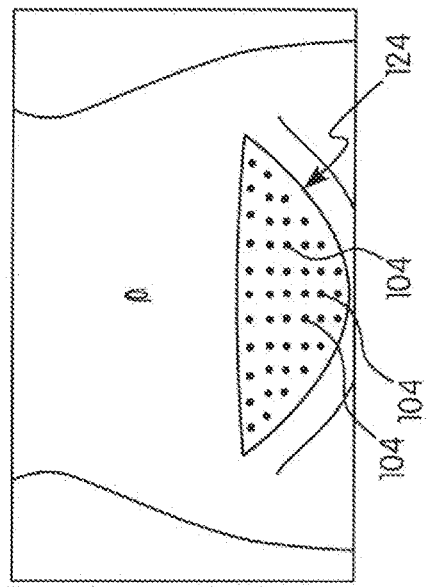
FIG. 11C depicts a procedure to treat belly conditions, according to an embodiment of the invention.

In another skin treatment, as depicted in FIG. 10, acne pimples can be treated. For acne pimple treatment, performing freeze-thaw cycles in the dermal layer will lead to permanent comedone removal. Comedones are associated with the pilosebaceous unit, which includes a hair follicle and sebaceous gland. These units are mostly on the face, neck, upper chest, shoulders and back. (Williams H, Dellavalle R, Garner, S. "Acne Vulgaris," *The Lancet* 379, No. 9813 (2012) 361-72.) Excess keratin combined with sebum can plug the opening of the follicle. This small plug is called a microcomedo. Androgens increase sebum (oil) production. If sebum continues to build up behind the plug, it can enlarge and form a visible comedo. A comedo may be open to the air ("blackhead") or closed by skin ("whitehead"). Being open to the air causes oxidation, which turns it black. Propionibacterium acnes are the suspected infectious agent in acne.

It can proliferate in sebum and cause inflamed postules (pimples) characteristic of acne. Nodules are inflamed, painful deep bumps under the skin. Comedones that are 1 mm or larger are called macrocomedones.

As depicted in FIG. 10, the base 118 of the hair follicle 120 is located in the dermis 110. Therefore, the needle portion 116 of the treatment device is inserted into the skin, through the epidermis 108, into the dermis 110 and into the base 118 of the hair follicle 120. Thus, the treatment zone 122, i.e., the area where the effects of the freeze-thaw cycles are experienced, extends from the skin surface into the dermis 110. The treatment zone 122 corresponds to the depth of needle insertion. Needle penetration into the dermis 110, induces necrosis of the hair follicle 120 and associated sebaceous gland when the freeze-thaw cycles are performed. Necrosis of the hair follicle 120 and sebaceous gland, prevents the comedone in this specific area from returning.

In order to treat: the double chin area (see FIG. 11A); bags under the eyes (see FIG. 11B); and anywhere else in the body where areas of fat are not proportional to fat in other areas of the body such as, for example, thighs, waists, arms, abdomen (see FIG. 11C), knees, male breasts (see FIG. 11D), etc., the freeze-thaw cycle treatment is performed down to the hypodermis layer 112. For these treatments, the treatment instrument needle should penetrate all the way into the hypodermis 112 such that the freeze-thaw cycling treatment is performed along the entire length of the needle that extends from the surface of the skin down to its distal end in the hypodermis. Similar to the previous described treatments, as depicted in FIGS. 11A-11D, multiple needle insertions 104 are performed in the target areas 124.

Performing freeze-thaw cycling in the hypodermal layer 112 leads to adipocyte cell reduction, which is beneficial when there is a need for local lipolysis in the hypodermis layer, for example. Treating the hypodermis as such causes adipocyte apoptosis as adipocyte cells are more sensitive to cold temperatures than the rest of the tissue in the other skin layers. (Manstein D, Laubach H, Watanabe K, Farinelli W, Zurakowski D, Anderson R. "Selective Cryolysis: A Novel Method of Non-Invasive Fat Removal," *Lasers in Surgery and Medicine* 40 (9) (2008) 595-604.)

Figure 12B:
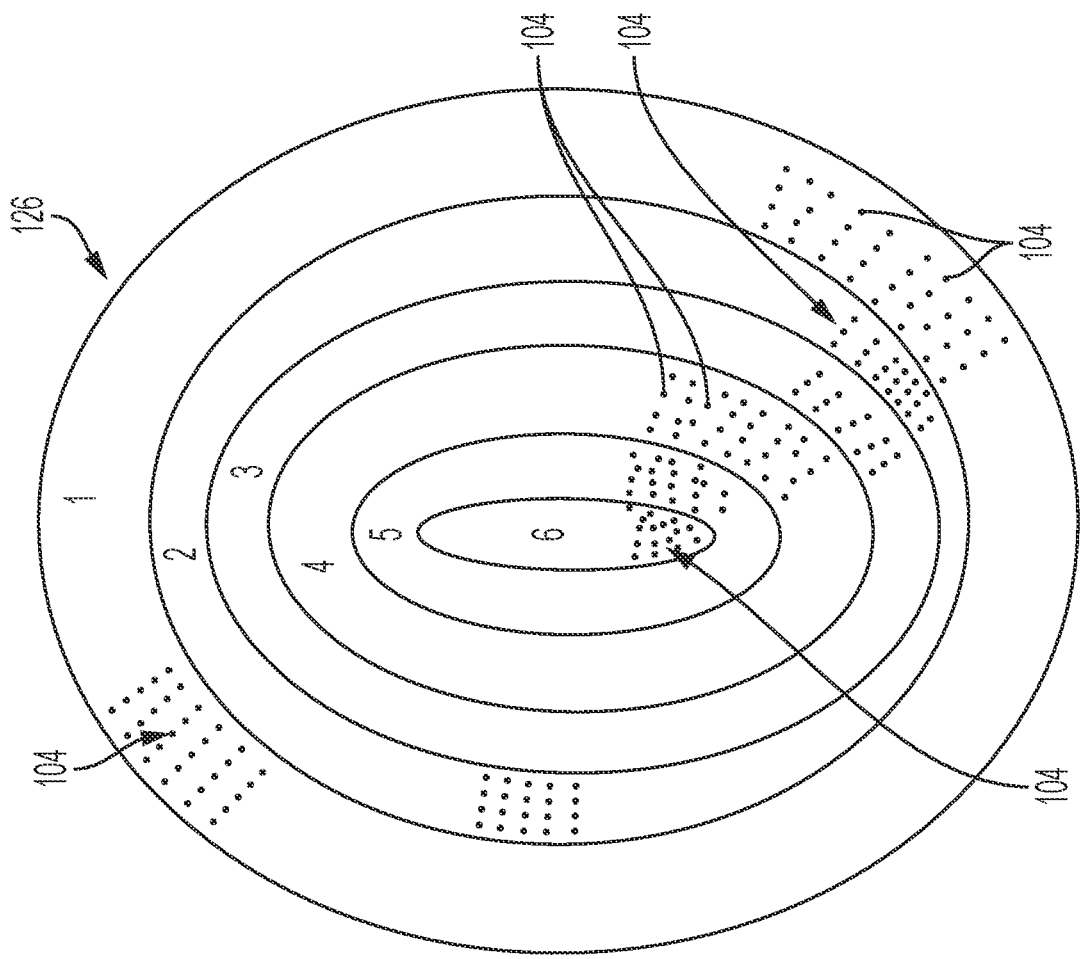
FIG. 12B depicts the varying depth of the fat layer in FIG. 12A.
Figure 12A:
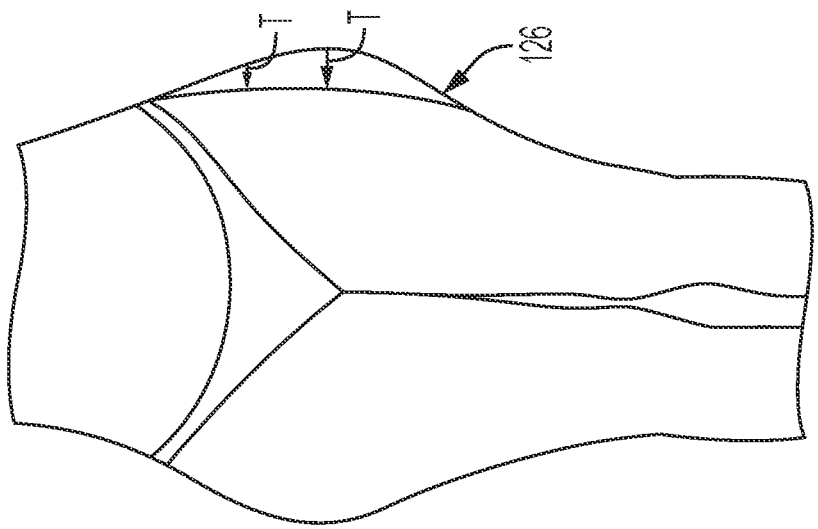
FIG. 12A depicts the fat layer in thigh areas, according to an embodiment of the invention.

In order to induce lipolysis of specific areas on the body and face, this system is used to apply freeze-heat cycle treatment to cover the area in which fat removal is desired (see FIGS. 11A-11D). The needle penetration depth is determined according to the thickness of the fat to be treated in the target area 124. As depicted in FIG. 12A, in some areas 126 of the body, the thickness "T" of the fat layer is not constant and varies in depth. Accordingly, in order to effectively treat these areas 126 and to have resulting skin that is smooth, the depth of needle insertion is be determined by the thickness "T" of the fat layer at each point where the freeze-thaw cycles will be performed. Depicted in FIG. 12A is a patient with a need for thigh lipolysis. Depicted in FIG. 12B is a side-view of the target area 126 in FIG. 12A with the varying depth of the fat layer identified by the different rings (1-6). As can be seen from FIG. 12A, the depth of the fat layer increases from ring 1 to ring 6. Accordingly, the depth of needle insertion in the area of the skin encompassed by ring 6 will be greater than the depth of insertion of the area of skin encompassed by ring 1. As previously disclosed, the depth of needle insertion can be controlled by adjusting the length that the needle extends past disk-like section 72 of the treatment device 48. Accordingly, it is important that the depth of the needle insertions 104 in the skin areas encompassed by each ring be deep enough to ensure complete lipolysis.

Figure 13:
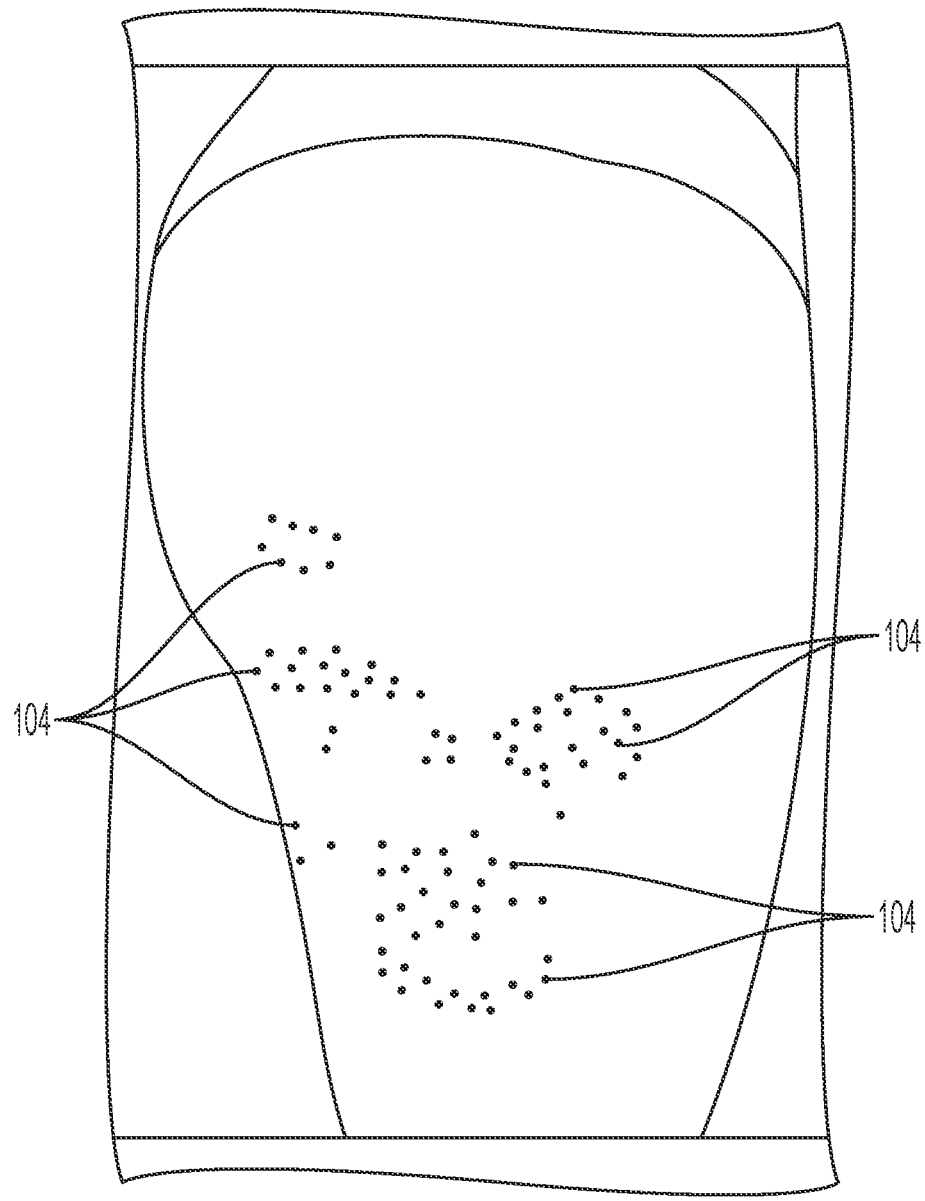
FIG. 13 depicts a procedure to treat cellulite, according to an embodiment of the invention.

Moreover, because performing the freeze-thaw cycling treatment in the hypodermal layer can result in very accurate and local lipolysis, this treatment can also be used to treat cellulite. Cellulite is located in the subsurface—or subcutaneous layer of the skin and is made up of connective tissue and fat cells known as the septa. Cellulite forms when the structural support of the skin starts to collapse and the fat cells push through, which causes the "dimpled" look. Performing the freeze-thaw treatment in these "dimpled" skin areas, reduces the fat cells that push through the connective tissue around the septa, which results in smoother skin in these areas. Thus, as can be seen in FIG. 13, multiple needle insertions 104 in the skin areas containing the cellulite are performed and multiple freeze-thaw cycles are performed for each needle insertion 104.

As previously disclosed, the freeze-thaw cycles are performed along the entire length of the needle that is inserted into the target tissue/skin area. As also previously disclosed, the length of the needle/depth of insertion and freezing temperatures will be determined based on the treatment being performed, both of which may be adjusted by the doctor performing the procedure. For example: if there is a need to apply this treatment only to the epidermis layer for sunspot treatment, the needle should penetrate only 0.5-1.5 mm into the skin as depicted in FIG. 9A; or if there is a need to perform this treatment only on the dermis layer in order to increase skin elasticity and eliminate wrinkles, scars, stretch marks, etc., the depth of the needle insertion should not exceed 3.5 mm as depicted in FIGS. 7 and 10. However, if there is a need to treat fat in the hypodermis layer 112, the depth of needle insertion is determined based on the thickness of the fat layer in the area to be treated, where the thickness of the fat layer and hence, the depth of needle insertion can range from approximately 5 mm to approximately 20 mm.

Figure 14:
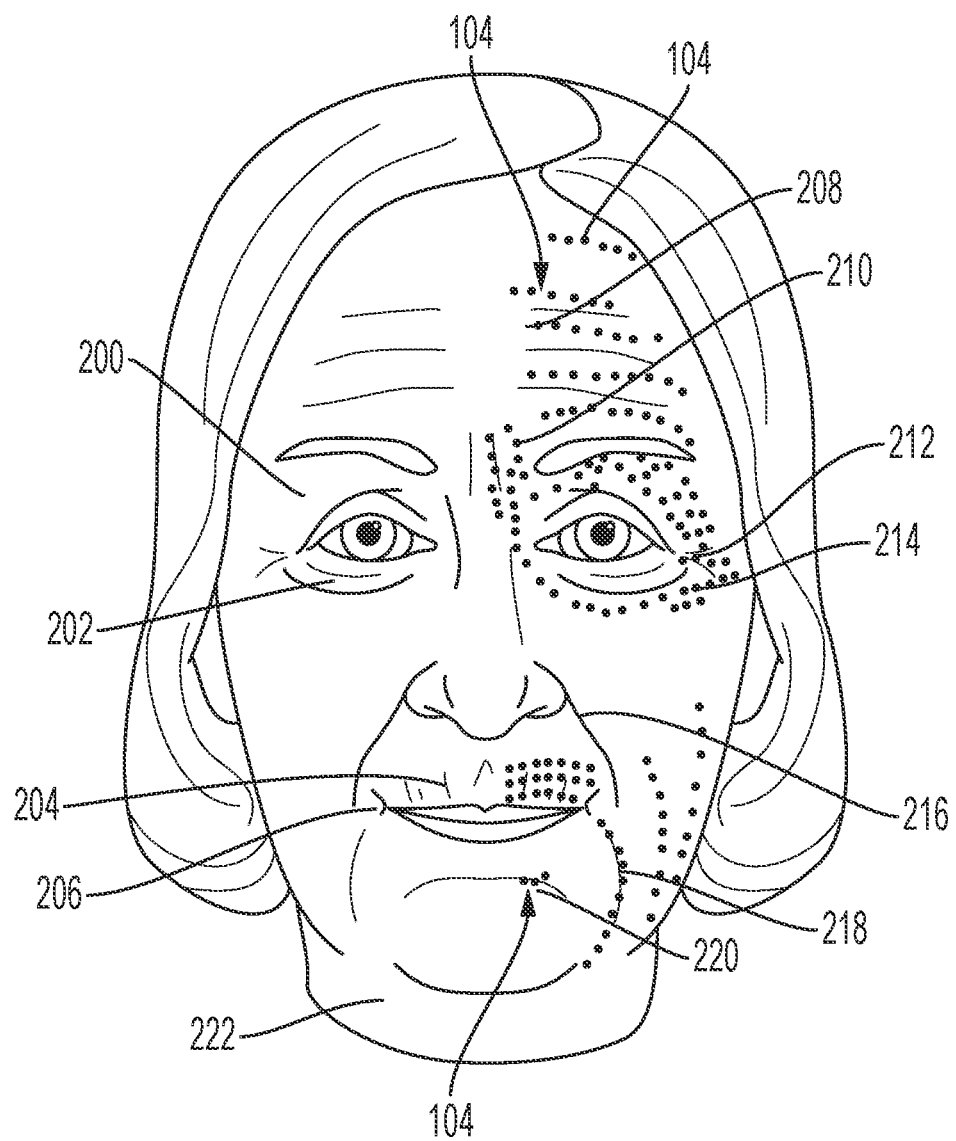
FIG. 14 depicts procedures to treat various facial skin conditions, according to an embodiment of the invention.

Depicted in FIG. 14 are additional skin conditions that can be treated with the embodiments of the system and treatment device disclosed herein. For example, freeze-thaw cycling can be used to treat: brow droop 200, bunny lines 202, vertical lip lines 204, mouth frown 206, forehead lines 208, frown lines 210, crow's feet 212, tear troughs 214, nasolabial folds 216, marionette lines/jowls 218, mental crease 220 and neck folds 22. Depicted on the left side of FIG. 14 are the skin conditions and depicted on the right side of FIG. 15 are the needle insertion 104 patterns necessary to treat such conditions with freeze-thaw cycling.

In addition, because the volume of the tissue is decreased during most of the treatment procedures disclosed and described herein, the overlying skin surface area will need to be reduced as well. Accordingly, performing the freeze-thaw cycles on all layers of the skin, results in an increase in the elasticity of the dermis allowing the dermis to more easily adapt to the reduced underlying tissue volume.

The foregoing disclosure provides for embodiments of systems, devices and methods for treating skin conditions such as, for example, wrinkles, skin pigmentation, areas with excessive fat, cellulite, etc. While several components, techniques and aspects have been described with a certain degree of particularity, it is manifest that many changes can be made in the specific designs, constructions and methodology herein above described without departing from the spirit and scope of this disclosure.

It is to be understood that the embodiments of the invention described herein are not limited to particular variations set forth herein as various changes or modifications may be made to the embodiments of the invention described and equivalents may be substituted without departing from the spirit and scope of the embodiments of the invention. As will be apparent to those of skill in the art upon reading this disclosure, each of the individual embodiments described and illustrated herein has discrete components and features that may be readily separated from or combined with the features of any of the other several embodiments without departing from the scope or spirit of the embodiments of the present invention. In addition, many modifications may be made to adapt a particular situation, material, composition of matter, process, process act(s) or step(s) to the objective(s), spirit or scope of the embodiments of the present invention. All such modifications are intended to be within the scope of the claims made herein.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. Additionally, numeric ranges are inclusive of the numbers defining the range, and any individual value provided herein can serve as an endpoint for a range that includes other individual values provided herein. For example, a set of values such as 1, 2, 3, 8, 9, and 10 is also a disclosure of a range of numbers from 1-10, from 1-8, from 3-9, and so forth.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A treatment instrument for treating body tissue, the treatment instrument comprising:
 a distal end;
 a proximal end;
 a connecting portion adjacent the proximal end;
 a needle element adjacent the distal end, the needle element including:
  a delivery channel,
  a return lumen circumscribing the delivery channel for delivering working fluid from the needle element, and
  a flow chamber in fluid communication with the delivery channel;
 a handle portion disposed between the proximal and distal end;
 a depth-limiting element to limit an injection depth of the needle element into body tissue;
 an adjustment device for adjusting the injection depth of the needle element; and
 a proximal section including:

a freeze lumen in fluid communication with the delivery channel for delivering cold working fluid to the flow chamber of the needle element, a thaw lumen in fluid communication with the delivery channel for delivering warm working fluid to the flow chamber of the needle element, and wherein the return lumen circumscribes the freeze lumen and the thaw lumen, and wherein the proximal end of the treatment instrument includes thermal insulation about an exterior thereof.

2. The treatment instrument of claim 1, wherein the adjustment device comprises a knob, a slider, or a dial.

3. The treatment instrument of claim 2, wherein the adjustment device is located on the handle portion.

4. The treatment instrument of claim 1, wherein the adjustment device changes a length of the needle element that extends from the depth-limiting element.

5. The treatment instrument of claim 1, further comprising a heating element.

6. The treatment instrument of claim 5, wherein the heating element is located adjacent to the needle element.

7. The treatment instrument of claim 5, wherein the heating element prevents freezing of body tissue adjacent an exterior surface of the body tissue being treated.

* * * * *